(12) United States Patent
Butler et al.

(10) Patent No.: US 6,380,449 B1
(45) Date of Patent: Apr. 30, 2002

(54) DEHYDROGENATION PROCESS

(75) Inventors: James R. Butler, Houston; James T. Merrill, Katy, both of TX (US); Adrian M. Jacobsen, Baton Rouge, LA (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 09/718,601

(22) Filed: Nov. 22, 2000

(51) Int. Cl.$^7$ .......................... C07C 5/367; F28D 21/00; B01J 10/00; B01J 8/04
(52) U.S. Cl. .................. 585/440; 585/444; 585/445; 585/443; 585/921; 585/922; 585/923; 585/924; 422/228; 422/205; 422/229; 422/197
(58) Field of Search .................. 585/440, 444, 585/445, 443, 921, 922, 923, 924; 422/228, 205, 229, 197

(56) References Cited

U.S. PATENT DOCUMENTS

| 4,134,908 A | * 1/1979 | Steiner et al. ............... 518/715 |
| 4,287,375 A | 9/1981 | Moller et al. ............... 585/440 |
| 4,549,032 A | 10/1985 | Moeller et al. ............. 585/445 |
| 5,358,698 A | 10/1994 | Butler et al. ................ 422/218 |
| 6,096,937 A | 8/2000 | Butler et al. ................ 585/440 |

* cited by examiner

Primary Examiner—Thuan D. Dang
(74) Attorney, Agent, or Firm—William D. Jackson

(57) ABSTRACT

Process for the catalytic dehydrogenation of ethylbenzene in which a feedstock containing ethylbenzene and steam is supplied into the inlet of a tubular reactor containing a dehydrogehation catalyst. Within the reactor, the feedstock flows through at least a portion of the reactor along a spiral flow path extending longitudinally of the reactor. The resulting styrene product is then recovered from a downstream or outlet section of the reactor. The spiral flow path through which the feedstock is passed is located at least adjacent the inlet side of the reactor and at least a portion of the spiral flow path contains a particulate dehydrogenation catalyst. The spiral flow path may extend throughout a major portion of the elongated tubular reactor and may contain a particulate dehydrogenation catalyst in a substantial portion there.

18 Claims, 6 Drawing Sheets

DEHYDROGENATION PROCESS

BACKGROUND OF THE INVENTION

The catalytic dehydrogenation of ethylbenzene to produce styrene is typically carried out at temperatures within the range of about 540–660° C. under near atmospheric or even subatmospheric pressure conditions. Typically, an ethylbenzene steam feed having a steam to ethylbenzene mole ratio of perhaps 7 or 8 or even higher is passed over a dehydrogenation catalyst such as iron oxide in an adiabatic dehydrogenation reactor. The dehydrogenation reactor may be of various configurations including a radial flow reactor such as disclosed in U.S. Pat. No. 5,358,698 to Butler et al or a linear or tubular reactor such as disclosed in U.S. Pat. Nos. 4,287,375 and 4,549,032, both to Moeller et al. As disclosed, for example in the aforementioned '032 patent to Moeller et al, an iron-oxide-based dehydrogenation catalyst is employed in a tubular reactor containing a plurality of reaction tubes which are heated by a hot molten salt bath.

Yet another reactor system for the catalytic dehydrogenation of ethylbenzene to produce styrene is disclosed in U.S. Pat. No. 6,096,937 to Butler et al. In the Butler et al system, a reactor system comprises a furnace structure which incorporates a plurality of internal reactor tubes which contain a dehydrogenation catalyst and which operate in an ascending heat mode. Here, the reactor system incorporates gas-fired heaters which heat the interior of the furnace to a temperature suitable for dehydrogenation to bring the temperature within the reactor tubes to the desired level by the application of heat which varies along the length of the tubes.

SUMMARY OF THE INVENTION

In accordance with the present invention, there is provided a process for the catalytic dehydrogenation of ethylbenzene in a tubular reactor. In carrying out the invention, a feedstock containing ethylbenzene and steam is supplied into the inlet of a tubular reactor containing a dehydrogenation catalyst. The tubular reactor is operated under temperature conditions effective to cause the dehydrogenation of ethylbenzene with the attendant production of styrene in the presence of the dehydrogenation catalyst. Within the reactor, the feedstock flows through at least a portion of the reactor along a spiral flow path extending longitudinally of the reactor. The resulting styrene product is then recovered from a downstream or outlet section of the reactor. Preferably, the spiral flow path through which the feedstock is passed is located at least adjacent the inlet side of the reactor, and at least a portion of the spiral flow path contains a particulate dehydrogenation catalyst. In a further embodiment of the invention, a spiral flow path extends throughout a major portion of the elongated tubular reactor and at least a substantial portion of the spiral flow path contains a particulate dehydrogenation catalyst. Preferably, the steam to styrene mole ratio of the feedstock is about 6 or less and more preferably within the range of about 5–6. The invention is particularly applicable to a variable heat (non-adiabatic) process in which heat is applied externally to the tubular reactor to provide an amount of heat which varies along the length of the tubular reactor.

In a further aspect of the invention, a feedstock containing ethylbenzene and steam is supplied into a plurality of tubular reactors located within the interior of a dehydrogenation reactor vessel. The tubular reactors are arranged in a parallel relationship relative to one another in which the tubular reactors are spaced laterally from one another and are spaced from the interior wall of the reaction vessel. The tubular reactors each have a mixing stage comprising a longitudinally-extending helical baffle providing a spiral flow path for mixing of the ethylbenzene and steam within the reactor. The interior of the reaction vessel is heated by a gas-fired or other suitable heating systems in order to provide a heating zone externally of the tubular reactor to provide an amount of heat which varies along the lengths of the tubular reactors. The supplied mixture of ethylbenzene and steam flows through the parallel tubular reactors into contact with a particulate dehydrogenation catalyst in the reactor under temperature conditions, resulting from the externally-applied heat, which are effective to cause the dehydrogenation of ethylbenzene to styrene in the presence of the dehydrogenation catalyst. Subsequent to the dehydrogenation reaction, the styrene product is recovered from the tubular reactors through outlets located downstream of the dehydrogenation catalyst.

In a further aspect of the invention, there is provided a reaction system for the catalytic reaction of a plurality of reactants in a feed stream. The reaction system comprises a plurality of parallel, elongated, tubular reactors having inlet and outlet sides. An inlet manifold is connected to the tubular reactors in order to supply a mixture of reactants to the inlet sides of the tubular reactors. The reactors incorporate a mixing section adjacent the inlet sides thereof, each reactor comprising at least one static baffle in an elongated helical configuration comprising a spiral flow path. A reaction section in each of the tubular reactors is located downstream of the initial mixing section and comprises a bed of catalyst particles. An outlet manifold is connected to the outlet side of the tubular reactors and is effective to supply reaction product from the tubular reactors to a suitable recovery system.

DETAILED DESCRIPTION OF THE INVENTION

The present invention may be carried out employing tubular reactors of any suitable configuration. Thus, a tubular reactor of the type disclosed in the aforementioned patent to Moeller et al may be employed. Preferably, however, the invention will be carried out employing tubular reactors employed within a electrically-heated or gas-fired furnace operated in a variable heat mode such as disclosed in U.S. Pat. No. 6,096,937 to Butler et al, and the invention will be described with reference to this reactor configuration. Thus, the reactor may be operated as an ascending heat reactor, as disclosed in the aforementioned '937 patent to Butler et al, or it may be operated as a relatively constant heat adiabatic reactor. Regardless of the nature of the operation of the system, the reactor tubes will incorporate a helical spiral flow mixing section as described in greater detail below.

Figure 1:
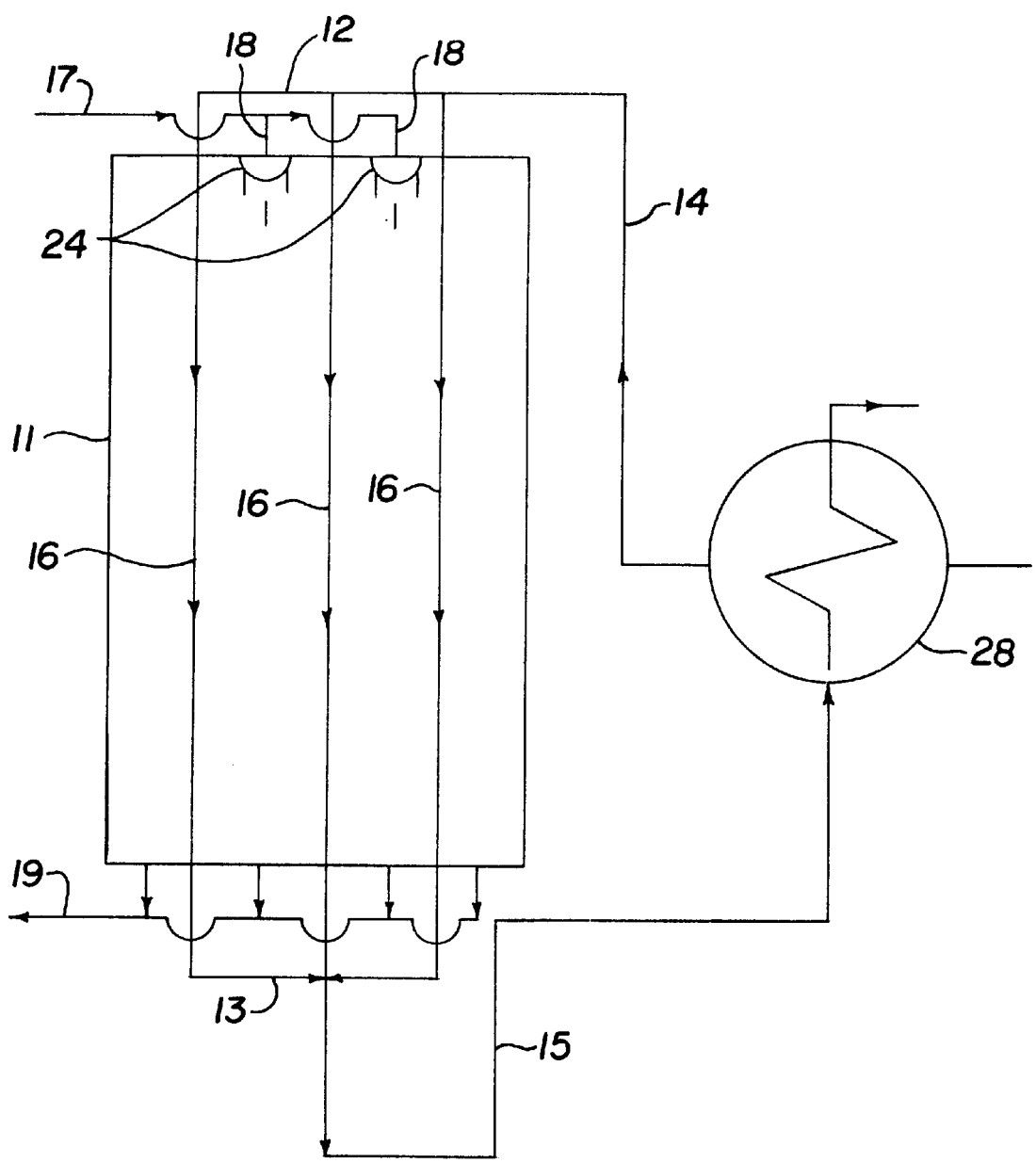
FIG. 1 is a schematic illustration of a reactor incorporating a plurality of tubular reactors for use in carrying out the present invention.

Referring initially to FIG. 1, there is shown a schematic illustration of an ascending-heat ethylbenzene reactor which is disclosed as having a reaction chamber defined by an external shell 11 and having an inlet manifold 12 and an outlet manifold 13. A supply line 14 is connected to inlet manifold 12 to supply an ethylbenzene-steam feed stock, and a product flow line 15 containing styrene and unreacted ethylbenzene and steam is connected to the outlet manifold 13.

The central section of the ethylbenzene reactor includes a furnace 11 inside which is located a series of reactor flow tubes 16 which are connected in parallel to the inlet manifold 12. The open bore of each tube 16 is exposed to the inlet manifold 12 to allow the ethylbenzene steam feed to enter through line 14 into inlet manifold 12 and to traverse tubes 16 into outlet manifold 13. Although, only three reactor tubes are disclosed in this schematic drawing, in actual practice a large multitude of such tubes normally would be provided in the reactor. A plurality of burners 18 are located at the top of the furnace shell. Burner tubes 18 are connected to a source of fuel such a natural gas, hydrogen, or other combustible gas which is provided by means of fuel inlet line 17 communicating with heater elements 18. A combustion products exhaust line 19 communicates through the wall of chamber 11 to carry the products of combustion from the flames of nozzles 24 of the heater elements. A source of oxygen may also be provided by means of a separate oxygen supply line or air supply line which may be connected to burner tubes 18 separately or may be passed through a mixer box prior to entering line 17 where air or oxygen can be mixed with the gaseous fuel.

In typical operation, an ethylbenzene feedstock (a mixture of ethylbenzene and steam) is provided through inlet line 14 and flows into the reactor tubes 16. The interiors of reactor tubes 16 may be completely or partially filled with a suitable EB dehydrogenation catalyst. Those skilled in the art are aware of suitable dehydrogenation catalysts which can be advantageously utilized in the present invention. The ethylbenzene feedstock flows from inlet header 12 through tubes 16 and across the chosen catalyst where it undergoes dehydrogenation to produce the resulting styrene product.

Concurrently with supply of the ethylbenzene feedstock, the gaseous mixture of fuel and oxygen source flows through line 17 and into heater nozzles 24. An ignition source is provided upon startup of the reactor and the gas is continuously passed through nozzles 24 and burns as it exits the nozzles. A minor amount of experimentation can determine the particular nozzle sizes to use for obtaining an ascending-heat thermal reactor. Thus, as ethylbenzene enters line 14 and passes through chamber inlet header 12 into reactor tubes 16, it is passed across the dehydrogenation catalyst contained in the reactor tubes 16 and subjected to an increasing level of heat input due to the gaseous fuel being consumed. Although gaseous fuel is desirable, it is, of course, possible to use a liquid fuel, which can be atomized by the oxygen source gas at a point prior to entering line 17. Other conventional nozzle-heater arrangements can be used with different fuel sources. In addition, it is possible that, rather than a chemically-driven heat supply, one could substitute electrical heating elements which vary in heat generation from the input end of the reactor to the output end of the reactor, to obtain the increasing heat supply for the reactor. Thus, one skilled in the art could substitute electrical heating elements for gas-fired heaters 18 with increasing heat output towards the end of the heating elements associated with the output end of the reactor tube 16.

Usually, it will be desirable to use a heat source that is compatible with the refining operations around the dehydrogenation reactor where the most available fuel is usually hydrogen or a compressed natural gas and therefore the description here is defined in terms of a gas-fired heating system. Upon traversing the length of reactor tubes 16 across the catalyst contained therein, a substantial dehydrogenation of the ethylbenzene feed is accomplished, and the product exiting into the outlet header contains substantial styrene, which is then passed through product flow line 15 to a heat exchanger 28 in indirect heat exchange with the feed stock in inlet line 14. From the heat exchanger, the dehydrogenation product is passed to a system (not shown) for further purification and removal of non-styrene products such as ethylbenzene, benzene, toluene, and hydrogen. As previously mentioned, the combustion gases exiting nozzle 24 flow out through gas exhaust conduit 19 in the bottom of the heater box. Thus is described a reactor for dehydrogenating ethylbenzene into styrene which is defined as an ascending-heat reactor to provide heat input for the endothermic ethylbenzene dehydrogenation reaction and, furthermore, to provide increasing amounts of heat toward the end of the dehydrogenation reaction as the components being reacted are being used up and the reaction equilibrium tends to shift to the left.

As described in the aforementioned Butler et al patent, various changes can be made in the described dehydrogenation reactor system. The flow rate in terms of the liquid hourly space velocity (LHSV) through the tubes can be changed by varying the diameter of the reactor tubes along their length. For example, the reactor tubes can be smaller at the inlet end and larger at the outlet end to provide a decreasing LHSV down the length of each reactor tube. For a further description of a suitable reactor system for the dehydrogenation of ethylbenzene employing an ascending heat mode of operation, reference is made to the aforementioned U.S. Pat. No. 6,096,937 to Butler et al, the entire disclosure of which is incorporated herein by reference.

It is to be recognized that the parallel reactor tube configuration of the type disclosed in the Butler et al '937 patent can be employed in adiabatic reaction systems of the type more conventionally used in the dehydrogenation of ethylbenzene to produce styrene. In any case, it will be advantageous in carrying out the invention to employ a plurality of parallel tubular reactors with appropriate manifolding at the inlet and outlet sides of the reactors as described, for example, in the '937 patent.

Figure 2:
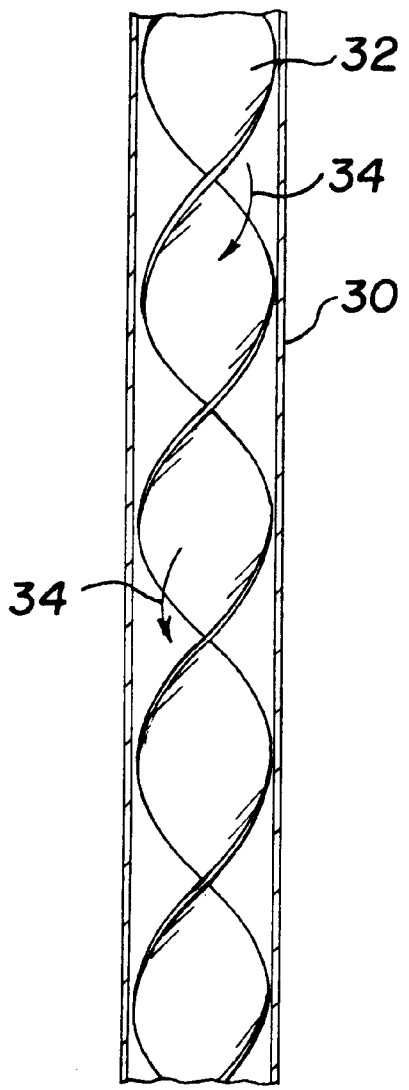
FIG. 2 is a perspective view with parts broken away of a static mixture incorporating a helical baffle providing a spiral flow path for the mixing of benzene and steam.

Turning now to FIG. 2, there is illustrated a preferred form of a static inline mixer which can be employed in carrying out the invention. FIG. 2 is a perspective view of a cylindrical static mixer employing a helical baffle to provide a spiral flow path along the length of the mixer. In FIG. 2, the mixer is shown with one-half of the outer cylindrical shell broken away to reveal the interior of the static mixture. As shown in FIG. 2, the mixer incorporates a cylindrical shell 30 with an internal helical baffle 32 providing a spiral flow path for the feedstock mixture as indicated by arrows 34. In the embodiment illustrated in FIG. 2, the baffle has a pitch of about 30° (from the longitudinal axis at the mixer) to provide for good mixing of the steam and ethylbenzene components and to provide for a relatively constant radial temperature gradient. That is, the temperature is relatively constant across the width of the mixer.

Figure 3:
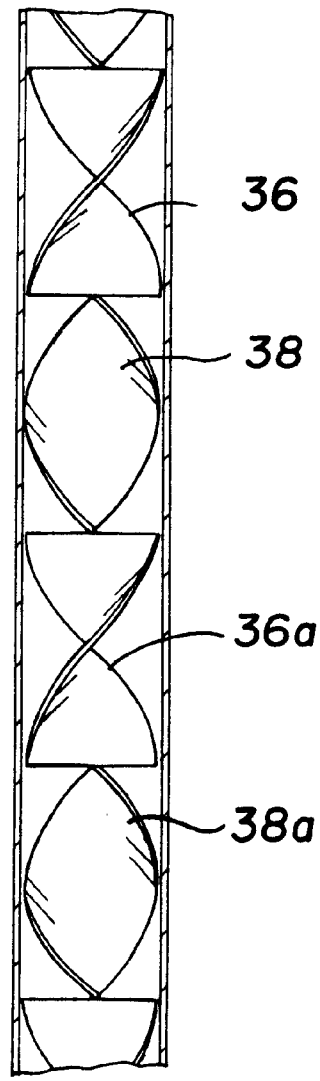
FIG. 3 is a perspective view of a modified form of a static mixture incorporating two flights of helical baffles.

While only a single or continuous helical baffle is employed in the mixer of FIG. 2, a further embodiment of the invention involves the use of an inline mixer having a plurality of helical baffle sections. A static mixer incorporating this embodiment of the invention is illustrated in FIG. 3, which is a perspective illustration, with parts broken away of a mixer having a first baffle section 36 and at least one second baffle section 38, which is angularly displaced (e.g., by 90° in the embodiment shown), with respect to the first baffle section 36, of a different pitch than the first baffle. This embodiment of the invention is particularly useful where the mixture is incorporated in only a portion of the tubular reactor as described below and provides for thorough and efficient mixing of the two components, initially after which a generally more linear flow takes place throughout the remainder of the tubular reactor. As an example of the embodiment illustrated in FIG. 3, baffle section 38 may be followed by baffle section 36a (displaced by 90°) followed in turn by baffle section 38a again displaced by 90°. In a further embodiment of the invention (not shown) one baffle may have a designated pitch with the other baffle having a different pitch.

Figure 4:
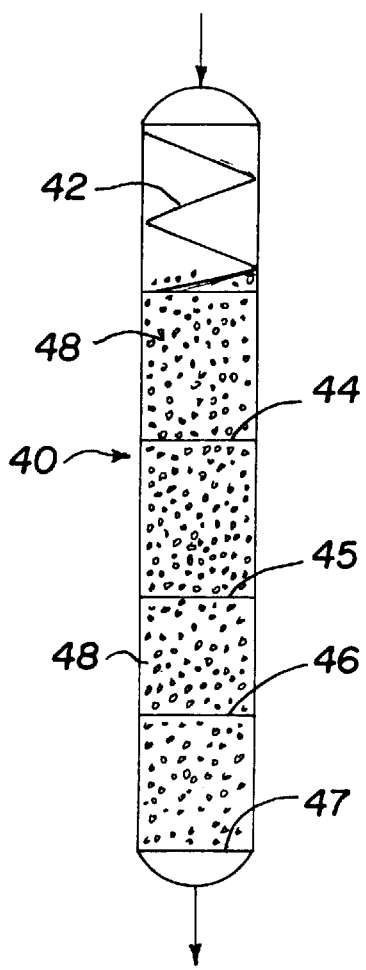
FIG. 4 is a schematic illustration of one form of tubular reactor configured with an initial spiral mixing section.

FIG. 4 is a schematic illustration with parts broken away of a tubular reactor configured with an initial helical flow mixing section with the remainder of the reactor packed with particulate dehydrogenation catalysts. While only a single tubular reactor is illustrated in FIG. 4 and in the following FIGS. 5 and 6, it is to be understood that a commercial dehydrogenation reactor will have a plurality of tubular reactors which are manifolded as described above with respect to the aforementioned '937 patent. For example, a commercial reactor implementing the present invention typically will contain from 500 to 1500 tubular reactors connected in parallel to suitable intake and exhaust manifolding systems. More particularly, and referring to FIG. 4, the tubular reactor contains an initial static mixing section 42 which conforms to the single baffle mixer illustrated in FIG. 2. In addition, the tubular reactor includes perforated grid plates 44, 45, 46, and 47 which support a particulate dehydrogenation catalyst 48 throughout the length of the tubular reactor and extending partially into the static mixture. Dehydrogenation catalyst 48 may be of any suitable type, typically constituting an iron oxide-based catalyst comprising iron oxide or a mixture of iron oxide with chromium oxide and sodium oxide, as disclosed in the aforementioned U.S. Pat. No. 4,549,032 to Moeller. As illustrated, the top portion of the reactor involving most of the length of the static mixture is free of catalysts in order to allow a spiral flow path of the reactants initially before contacting the dehydrogenation catalysts. However, the dehydrogenation catalyst may extend further upwardly and be packed in most or even all of the initial static mixture.

Figure 5:
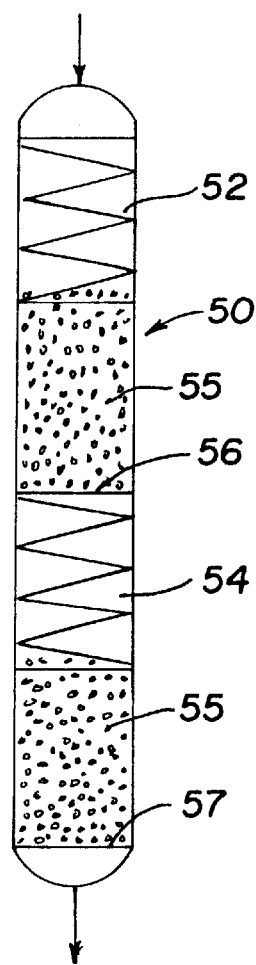
FIG. 5 is a schematic illustration of another embodiment of the invention incorporating several spaced mixing stages.

FIG. 5 illustrates another embodiment of the invention in which a tubular reactor 50 incorporates two spaced mixing stages, an initial mixing stage 52 and a second spaced and intermediate mixing stage 54. Catalyst particles 55 are interposed on suitable grid plates 56 and 57 above and below the intermediate mixing section 54. Sections 52 and 54 may be identical and different and may be single baffle static mixers as disclosed in FIG. 2 or multi-baffle mixers of the type described above with respect to FIG. 3. As before, the catalyst particles extend upwardly into a lower portion of the baffle mixing section 52. Similarly, the catalyst particles supported on grid 57 extend upwardly, partially into the mixing section 54 to encompass at least a lower portion of this mixing section. Alternatively, the particulate dehydrogenation catalyst may extend throughout the lengths of one or both of mixing sections 52 and 54.

Figure 6:
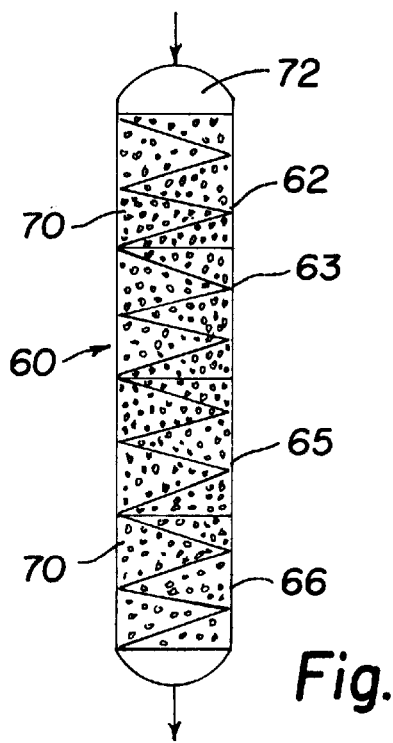
FIG. 6 is a schematic illustration of yet another embodiment of the invention incorporating helical baffles extending throughout a substantial length of tubular reactor.

FIG. 6 illustrates yet another embodiment of the invention in which all or at least a predominant portion of the longitudinal dimension of the tubular reactor incorporates one or more helical baffles providing one or more spiral flow paths throughout the length of the tubular reactor. In this embodiment of the invention, a tubular reactor 60 incorporates a series of static mixers 62, 63, 65, and 66, each corresponding to a mixer of the type illustrated in FIG. 2, disposed along the length of the tubular reactor. Each of the mixing sections is packed with a particulate dehydrogenation catalyst 70 with the initial mixer preferably containing catalysts in only a lower portion of the mixing section 62, similarly, as described above with respect to FIG. 4. Alternatively, the catalyst can extend upwardly through most or all of the initial static mixer or even into the plenum area 72 above the mixer 62. In FIG. 6, a spiral flow path is provided throughout substantially the length of the tubular reactor. While in the embodiment illustrated this is provided by a plurality of mixing sections stacked one on top of the other, it will be recognized that a continuous helical baffle can be provided by a single helix extending throughout the length of the tubular reactor.

The present invention, through the use of an inline static mixing section encompassing all or a portion of the tubular reactor, offers significant advantages in terms of selectivity to styrene production and in terms of the possibility of relatively low steam to hydrocarbon mole ratio (SHR).

In experimental work respecting the present invention, tests were carried out in an 8-inch diameter tubular reactor having an overall length of about 14 feet and a total catalyst length of 10 feet. The tests were carried out employing equal amounts of an iron oxide-based dehydrogenation catalyst using two types of static mixing schemes. In one set of tests, linear flow mixing was synthesized through the use of spaced beds of chrome molybdenum steel cylindrical particles, and in the other set of tests simulating the present invention, spiral flow static mixtures of the type illustrated in FIG. 2 were employed. In the first set of tests, the iron oxide-based catalyst in the form of 5.5 millimeter diameter cylinders of about 8 mm in length were loaded into the 8-inch diameter tube with 6 mixers of chrome molybdenum steel cylindrical particles interposed between the successive beds of catalysts. The mixers of chrome molybdenum steel cylindrical particles were formed by 3-inch thick beds formed of 1-inch diameter by 1-inch long chrome-moly cylindrical particles. Thus, in this set of experimental work the catalyst particles were loaded into the reactor to provide a column of catalyst particles of about 1–½ feet followed by 3 inches of the chrome-moly particles followed again by about 1–½ feet of catalyst particles. This sequence of catalyst particles and chrome-moly cylindrical particles was repeated until the sixth chrome-moly particle mixing bed was in place. Thereafter, additional catalyst was added until a total of about 3.5 cu. ft of catalysts were in place in the tubular reactor. In the second set of tests simulating the practice of the present invention, four 2-foot sections of static mixers incorporating a helical baffle as depicted in FIG. 2, were loaded into the 8-inch diameter tube. The catalyst loading was carried out by placing the initial 2-foot section of mixer into the tube and then filling this section with catalyst and then repeating this procedure with a second, third, and fourth placement of 2-foot sections of mixers. Additional catalyst was added after the final mixer was in place to bring the catalyst bed to about 20 inches below the top of the tubular reactor and provide an amount of catalyst equal to the amount of catalyst employed in the first set of experimental tests. The tests were carried out at a linear hourly space velocity (LHSV) of 1.4 hr.$^{-1}$ and an SHR ranging from 4:1 molar to about 9.5:1 molar. An electrically-powered feed heater was used to control the catalyst bed inlet temperature at the desired value. The temperature was controlled so that the outlet temperature was varied from values ranging from about 1100° to about 1120° F.

Figure 7:
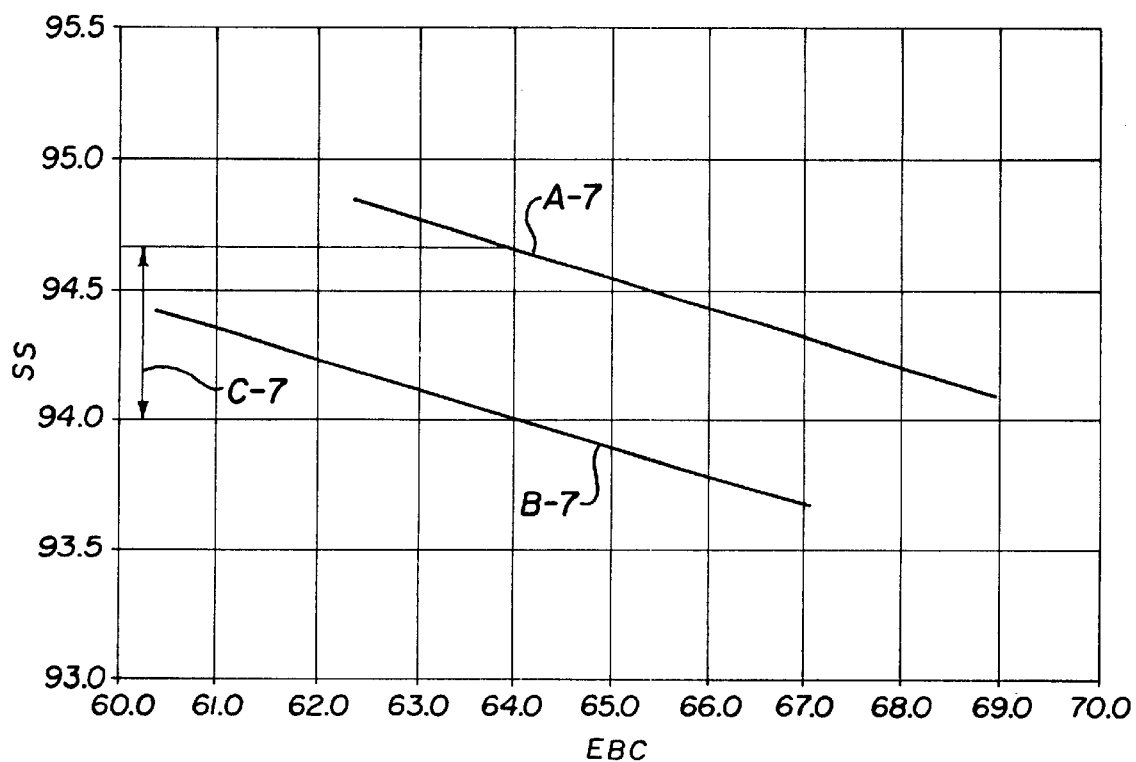
FIG. 7 is a graphical presentation showing the relationship between styrene selectivity and ethylbenzene conversion for a procedure incorporating the present invention in comparison with a relatively linear mixing system.
Figure 8:
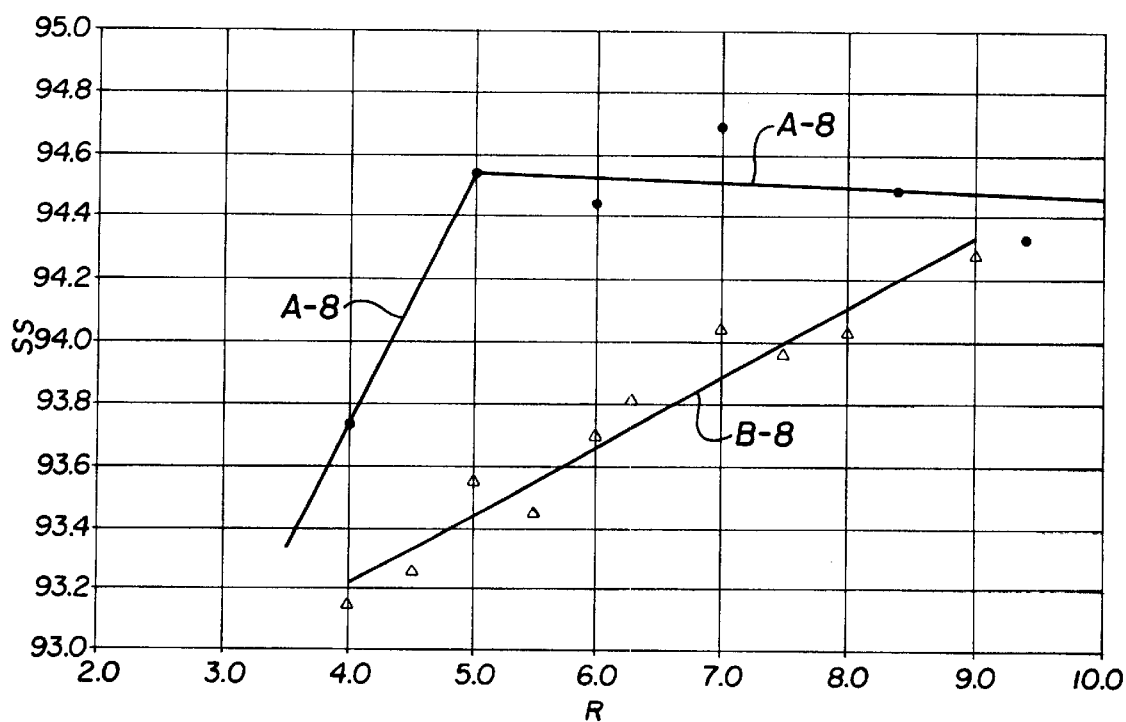
FIG. 8 is a graphical representation showing the relationship between styrene selectivity and the steam to hydrocarbon ratio for the two systems depicted in FIG. 7.
Figure 9:
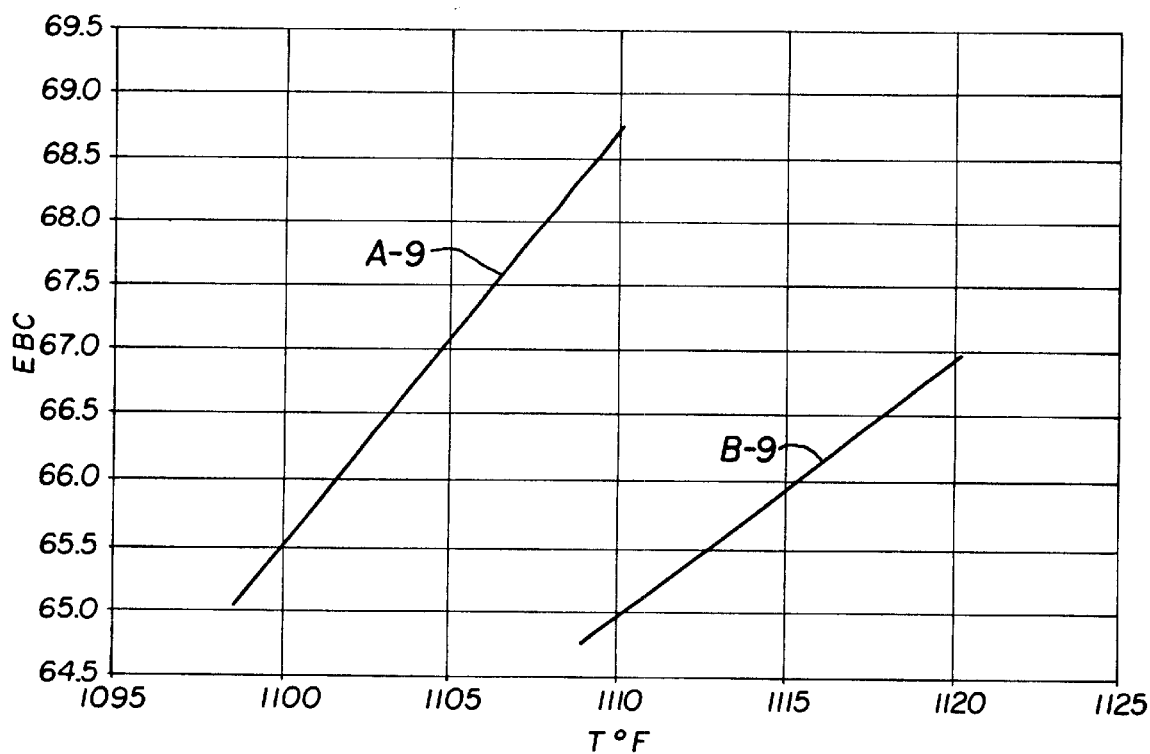
FIG. 9 is a graphical representation showing the relationship between ethylbenzene conversion and reaction temperature for the two modes of operation depicted in FIGS. 7 and 8.

The results of this experimental work are shown in FIGS. 7, 8, and 9. Turning first to FIG. 7, this is a graph illustrating styrene selectivity SS in wt. % plotted on the ordinate versus ethylbenzene conversion (EBC) in wt. % plotted on the abscissa. In FIG. 7, the results for Protocol A (employing the static mixers corresponding to those shown in FIG. 2) for a SHR values of 8 and 10 are indicated by curve A-7. The test results obtained using the beds of chrome-moly tubes (Protocol B) are indicated by curve B-7 for SHR values of 8 and 10. As can be seen from an examination of the data set forth in FIG. 7, Protocol A, simulative of the present invention, showed a consistent increase in styrene selectivity over ethylbenzene conversion rates ranging from about 62 to 68 wt. %. The use of the inline helical mixer in Protocol A showed a selectivity increase of about 0.7% as indicated by line segment C-7 in FIG. 7.

FIG. 8 is a graph showing styrene selectivity (SS) in wt. % plotted on the ordinate versus the SHR mole ratio (R) plotted on the abscissa. In FIG. 8 the selectivity observed for Protocol A is indicated by the ● data points and curve A-8. Similar data points for Protocol B are indicated by Δ and curve B-8. As indicated, Protocol A showed a consistently better selectivity than Protocol B over a wide range of steam hydrocarbon ratios. More importantly, the selectivity for Protocol A remains relatively good at SHR values down to 5:1. When the SHR is decreased further down to 4:1 mole ratio, a substantial decrease in performance is observed, but selectivity still remains better for Protocol A than for Protocol B. The effectiveness of Protocol A at relatively low steam to ethylbenzene ratios within the range of about 5 to 7 and especially within the range of about 5 to 6 is very significant since it enables operation at low SHR values with substantial decrease in capital and operating costs.

A further advantage of the present invention resides in the use of the static inline spiral mixing protocol providing somewhat lower operating temperatures than with the linear flow mixers. This is illustrated in FIG. 9 which is a graph of ethylbenzene conversion (EBC) in wt. % plotted on the ordinate versus the outlet temperature (T) in degrees Fahrenheit plotted on the abscissa. In FIG. 9, curve A-9 illustrates the results for Protocol A versus the results for Protocol B as indicated by curve B-9. As can be seen from an examination of FIG. 9, Protocol A consistently provided for an outlet temperature which was about 10–15° cooler than Protocol B at equal ethylbenzene conversion levels.

The present invention can be employed incorporating any suitable dehydrogenation catalyst suitable for the dehydrogenation of ethylbenzene. Such catalysts normally incorporate iron oxide along with secondary components such as chrome oxide as well as other inorganic materials and are typically formulated with a binder in particle sizes of about ⅛-inch. One suitable catalyst for use in carrying out the present invention is iron oxide catalyst promoted with potassium carbonate plus trace metals for selectivity enhancement available from Criterion Catalyst Company under the designation "Flexicat Yellow."

Having described specific embodiments of the present invention, it will be understood that modifications thereof may be suggested to those skilled in the art, and it is intended to cover all such modifications as fall within the scope of the appended claims.

What is claimed:

1. A process for the production of styrene by the catalytic dehydrogenation of ethylbenzene comprising:
    a. supplying a feedstock containing ethylbenzene and steam into a tubular reactor containing a dehydrogenation catalyst;
    b. operating said tubular reactor under temperature conditions effective to cause the dehydrogenation of ethylbenzene to styrene in the presence of said dehydrogenation catalyst;
    c. flowing said feedstock within at least a portion of said reactor along a spiral flow path located within an extending longitudinally of said reactor; and
    d. recovering styrene product from a downstream section of said reactor.

2. The process of claim 1 wherein said feedstock is passed along said spiral flow path at a location adjacent the inlet side of said reactor.

3. The process of claim 1 wherein at least a portion of said spiral flow path contains a particulate dehydrogenation catalyst.

4. The process of claim 1 wherein the steam to ethylbenzene mole ratio of said feedstock is about 10 or less.

5. The process of claim 1 wherein the steam to ethylbenzene mole ratio of said feedstock is within the range of 5–6.

6. The process of claim 1 wherein said spiral flow path extends throughout a major portion of the length of the elongated tubular reactor and at least a portion of said spiral flow path contains a particulate dehydrogenation catalyst.

7. A process for the production of styrene by the catalytic dehydrogenation of ethylbenzene comprising:
    a. supplying a feedstock containing ethylbenzene and steam into a tubular reactor having a mixing section comprising a longitudinally-extending helical baffle inside the tubular reactor providing a spiral flow path for the mixing of said ethylbenzene and steam;
    b. heating said tubular reactor by applying heat externally of said tubular reactor to provide an amount of heat which varies along the length of the tubular reactor;
    c. supplying said mixed steam and ethylbenzene into contact with a particulate dehydrogenation catalyst in said tubular reactor under temperature conditions effective to cause the dehydrogenation of ethylbenzene to styrene in the presence of said dehydrogenation catalyst; and
    d. recovering styrene product from said reactor through an outlet downstream of said dehydrogenation catalyst.

8. The process of claim 7 wherein said mixing section incorporates a second helical baffle having a pitch different from the pitch of said first recited helical baffle.

9. The process of claim 7 wherein said feedstock is passed along said spiral flow path at a location adjacent the inlet side of said reactor.

10. The process of claim 7 wherein at least a portion of said spiral flow path contains a particulate dehydrogenation catalyst.

11. The process of claim 7 wherein said helical baffle extends throughout a major portion of the length of the elongated tubular reactor to provide said spiral flow path and at least a portion of said spiral flow path contains a particulate dehydrogenation catalyst.

12. The process of claim 7 wherein the steam to ethylbenzene mole ratio of said feedstock is about 10 or less.

13. The process of claim 7 wherein the steam to ethylbenzene mole ratio of said feedstock is about 6 or less.

14. A process for the production of styrene by the catalytic dehydrogenation of ethylbenzene comprising:
   a. supplying a feedstock containing ethylbenzene and steam into a plurality of tubular reactors located within the interior of a dehydrogenation reactor vessel and arranged in a parallel relationship with respect to one another in which the tubular reactors are spaced from one another and spaced from the interior wall of the reaction vessel, each of said tubular reactor having a mixing stage comprising a longitudinally-extending helical baffle inside said each of tubular reactors providing a spiral flow path for mixing of said ethylbenzene and steam;
   b. heating the interior of said reaction vessel to provide heat externally of said tubular reactor to provide an amount of heat which varies along the lengths of the tubular reactors;
   c. within said tubular reactors, supplying said mixed steam and ethylbenzene into contact with a particular dehydrogenation catalyst in said tubular reactors under temperature conditions resulting from the externally applied heat, effective to cause the dehydrogenation of ethylbenzene to styrene in the presence of said dehydrogenation catalyst; and
   d. recovering styrene product from said tubular reactors through outlets of said tubular reactors.

15. The process of claim 14 wherein the mixing stages of said tubular reactors providing said spiral flow paths are located at least adjacent the inlets of said tubular reactor.

16. The process of claim 14 wherein the spiral flow paths of said reactors extend throughout major portions of the lengths of the elongated tubular reactors and at least a portion of said spiral flow paths contain a particulate dehydrogenation catalyst.

17. The process of claim 16 wherein the steam to ethylbenzene mole ratio of said feedstock is about 10 or less.

18. The process of claim 17 wherein the steam to ethylbenzene mole ratio of said feedstock is within the range of 5–6.

* * * * *